(12) United States Patent
O'Lenick et al.

(10) Patent No.: US 8,192,727 B1
(45) Date of Patent: Jun. 5, 2012

(54) SORBITOL POLYESTERS HAVING LIQUID AND SOLID DOMAINS

(75) Inventors: Kevin A. O'Lenick, Dacula, GA (US); Andrew J. O'Lenick, Dacula, GA (US); Anthony J. O'Lenick, Jr., Dacula, GA (US)

(73) Assignee: Surpa Tech Corporation, Lawrenceville, GA (US)

( * ) Notice: Subject to any disclaimer, the term of this patent is extended or adjusted under 35 U.S.C. 154(b) by 392 days.

(21) Appl. No.: 12/653,457

(22) Filed: Dec. 16, 2009

Related U.S. Application Data

(60) Provisional application No. 61/270,579, filed on Jul. 13, 2009.

(51) Int. Cl.
*A61K 8/02* (2006.01)
*C07C 69/347* (2006.01)

(52) U.S. Cl. ............... 424/70.11; 424/401; 528/295.3; 528/300; 528/301; 528/306; 524/100; 524/315; 524/547

(58) Field of Classification Search ............... 424/70.11; 524/306, 315, 100, 547; 528/295.3, 300, 528/301, 306
See application file for complete search history.

(56) References Cited

U.S. PATENT DOCUMENTS

| 6,800,275 | B1 * | 10/2004 | O'Lenick, Jr. ............ 424/70.11 |
| 7,473,707 | B1 | 1/2009 | O'Lenick |

* cited by examiner

*Primary Examiner* — Anoop Singh
*Assistant Examiner* — Anna Falkowitz

(57) ABSTRACT

The present invention is directed to a series of sorbitol esters that have two different molecular weight ester chains, one solid and one liquid, which when combined into a single molecule make a polymer that is solid, but has very unique flow properties. These materials find applications as additives to formulations in personal care products where there is a desire to have a structured film (provided by the solid fatty group) and flow properties, (provided by the liquid fatty group). These compounds by virtue of their unique structure provide outstanding skin feel.

8 Claims, No Drawings

SORBITOL POLYESTERS HAVING LIQUID AND SOLID DOMAINS

RELATED APPLICATIONS

This application claims priority to and benefit of U.S. Provisional Application No. 61/270,597 filed Jul. 13, 2009, the disclosure of which is incorporated herein for all purposes.
Federal Sponsorship
There is no federal sponsorship on the present invention.

FIELD OF THE INVENTION

The present invention is directed to a series of sorbitol esters that have two different molecular weight ester chains, one solid and one liquid, which when combined into a single molecule make a polymer that is solid, but has very unique flow properties. These materials find applications as additives to formulations in personal care products where there is a desire to have a structured film (provided by the solid fatty group) and flow properties, (provided by the liquid fatty group). These compounds by virtue of their unique structure provide outstanding skin feel.

BACKGROUND OF THE INVENTION

Sorbitan esters are known. They are derived from a cyclic material called Sorbitan derived from the dehydration of sorbitol. Sorbitan conforms to the following structure:

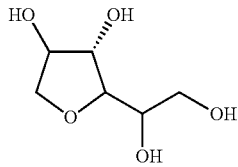

Sorbitan is esterified using fatty acids to make sorbitan esters. A typical sorbitan ester is shown:

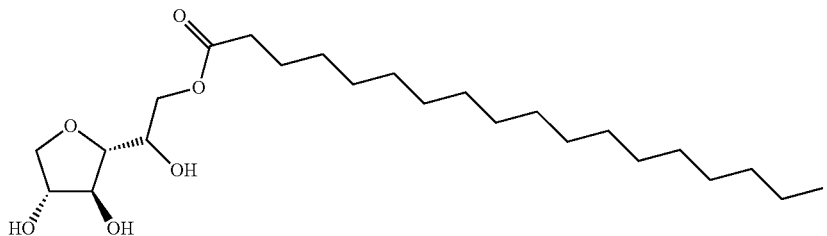

Sorbitan esters with different kinds of fatty acids and various degrees of esterification are known. Those are generally used as emulsifier for example in making cream.

Sorbitol, one of the reactants used to make the compounds of the present invention is linear. It contains six hydroxyl groups as shown below:

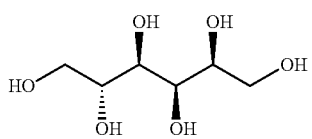

It is known that sorbitan fatty acid esters can be produced by direct, base-catalyzed reaction of sorbitol with a fatty acid at elevated temperatures.

U.S. Pat. No. 2,390,395 to Soltzberg describes the preparation of monoanhydro sorbitol which is rich in 1,4-sorbitan by anhydrization of sorbitol under reduced pressure at 120°-150° C. in the presence of an acid catalyst.

U.S. Pat. No. 2,387,842 to Soltzberg discloses the preparation of "sorbide" by heating sorbitol solution at reduced pressure (88-95 mm of mercury absolute) in the presence of an acid catalyst (sulfuric acid) until 2 moles of water per mole of sorbitol are removed.

U.S. Pat. No. 6,384,248 to O'Lenick, Jr. discloses Meadowfoam based sorbitan esters U.S. Pat. No. 6,013,813 to O'Lenick Jr. discloses Guerbet acid based sorbitan esters.

The patents referenced disclose sorbitan derivatives.

U.S. Pat. No. 7,473,707 to O'Lenick et al discloses specific alkoxylated sorbitan esters (Spider Esters) useful in delivering skin actives.

None of these patents provide polyester derivatives of mixed fatty esters of sorbitol as envisioned by the present invention.

THE INVENTION

Objective of the Invention

The present invention has as its objective a series of sorbitan polyesters that have both liquid and solid fatty groups contained thereon and are crosslinked by dimer acid.

The present invention also has an objective a process for treating hair and skin with the sorbitan polyesters that have both liquid and solid fatty groups contained thereon and are crosslinked by dimer acid.

Other objectives will become clear as one reads the specification and claims herein.

SUMMARY OF THE INVENTION

The present invention discloses a polyester made by the reaction of a mixture of liquid and solid fatty acids reacted with sorbitol and dimer acid.

DETAILED DESCRIPTION OF THE INVENTION

The present invention relates to a polyester that conforms to the following structure:

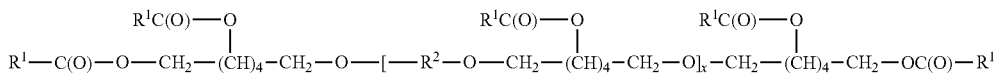

$R^1$ is a mixture of between 15 and 60%-$(CH_2)_a$-$CH_3$ and between 85 and 40% of fatty acids selected from the group consisting of

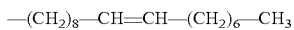

and

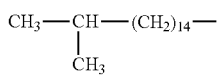

and mixtures thereof
a is an integer ranging from 14 to 20;
$R^2$ is selected from the group consisting of;

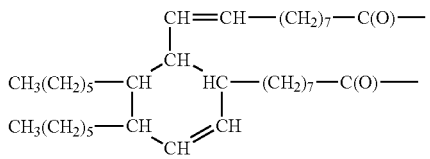

hydrogenated dimer acid, conforming to the following structure:

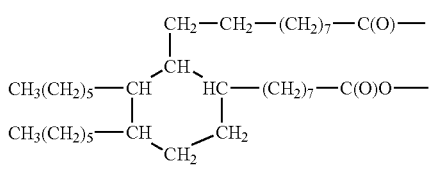

and mixtures thereof;
x is an integer ranging from 1 to 20.

Another aspect of the present invention is a process for conditioning hair and skin which comprises contacting the hair or skin with an effective conditioning concentration of a polyester that conforms to the following structure:

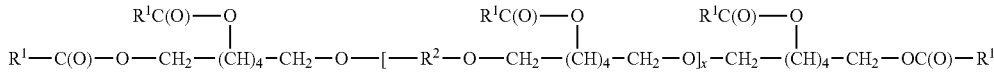

$R^1$ is a mixture of between 15 and 60% —$(CH_2)_a$—$CH_3$ and
between 85 and 40% of fatty acids selected from the group consisting of

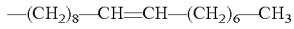

and

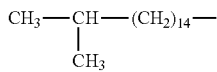

and mixtures thereof;

a is an integer ranging from 14 to 20;
$R^2$ is selected from the group consisting of;

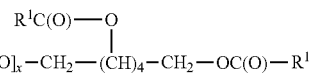

hydrogenated dimer acid, conforming to the following structure:

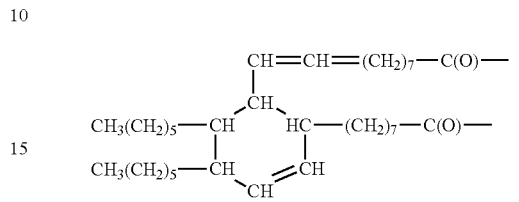

and mixtures thereof;
x is an integer ranging from 1 to 20.

In a preferred embodiment said effective conditioning concentration ranges from 0.1% to 20% by weight.

The products of the present invention are made by the esterification reaction of:

(a) sorbitol conforming to the following structure:

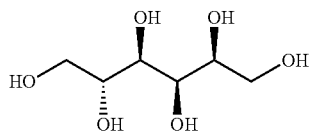

(b) a di acid selected from the group consisting of:

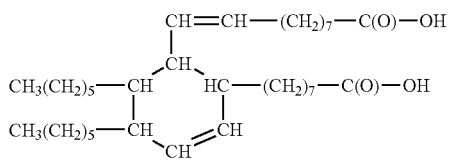

hydrogenated dimer acid, conforming to the following structure:

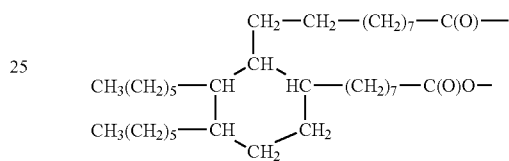

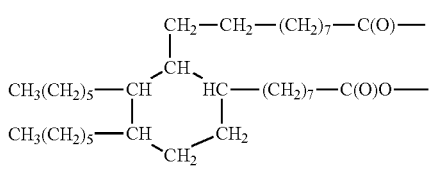

and mixtures thereof;
(c) a fatty acid that is liquid at room temperature, selected from the group consisting of oleic acid conforming to the following structure:

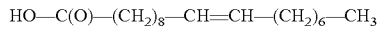

and iso-stearic acid conforming to the following structure:

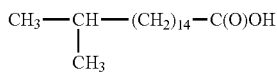

and mixtures thereof;
(d) a fatty acid that is solid at room temperature

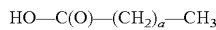

a is an integer ranging from 14 to 20.

Another aspect of the present invention is a process for conditioning hair and skin which comprises contacting the hair or skin with an effective conditioning concentration of a polyester made by the esterification reaction of:
(a) sorbitol conforming to the following structure:

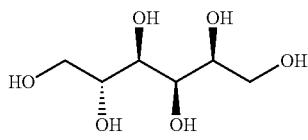

(b) a di acid selected from the group consisting of:

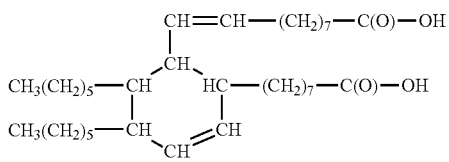

hydrogenated dimer acid, conforming to the following structure:

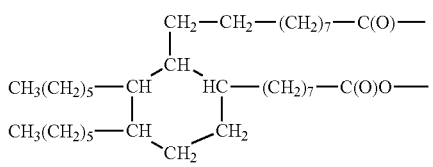

and mixtures thereof;
(c) a fatty acid that is liquid at room temperature, selected from the group consisting of oleic acid conforming to the following structure:

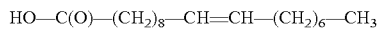

and iso-stearic acid conforming to the following structure:

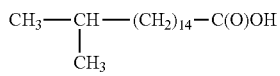

and mixtures thereof;
(d) a fatty acid that is solid at room temperature

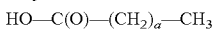

a is an integer ranging from 14 to 20.

Where there are two different types of ester group present, one liquid and one solid, the resulting structure cannot crystallize completely, since the liquid domains in the polymer act as molecular crystal distorters, resulting in a polymer that although having the same melting point, flows more easily when pressure is applied. The resulting solid will be soft and flowable, rather than hard and un-yielding.

EXAMPLES

Example 1

Sorbitol

Sorbitol is an item of commerce commercially available from a variety of sources. It conforms to the following structure:

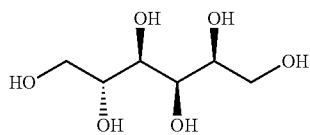

The IUPAC name for sorbitol is d-glucitol. The IUPAC name is (2R,3R,4R,5S)-hexane-1,2,3,4,5,6-hexol. CAS number 98201-93-5.

Examples 2-3

Example 2

Dimer Acid

Dimer acid is an item of commerce commercially available from a variety of sources. It conforms to the following structure:

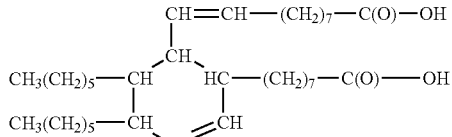

The CAS NUMBER is 61788-89-4.

Example 3

Hydrogenated Dimer Acid

Hydrogenated dimer acid, is an item of commerce available from a variety of sources conforming to the following structure:

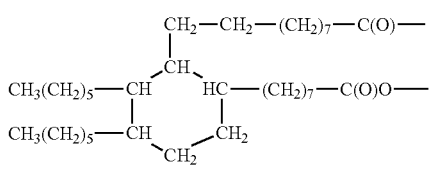

The CAS number is 68783-41-5

Example 4

Oleic acid

Oleic acid is an item of commerce available from a variety of sources. It conforms to the following structure;

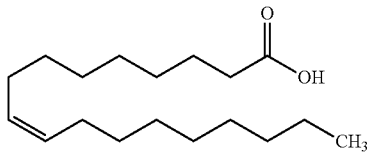

The CAS No. is 112-80-1.

Example 5

Iso-Stearic Acid iso-stearic acid is an item of commerce available from a variety of sources. It conforms to the following structure;

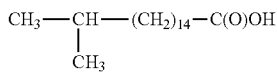

The CAS number is 2724-58-5.

Examples 6-9

Fatty Acids that are Solid at Room Temperature

These acids are an item of commerce available from a variety of sources. It conforms to the following structure;

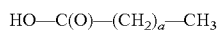

a is an integer ranging from 14 to 20.

| Example | a | Common Name | MW |
|---|---|---|---|
| 6 | 14 | palmitic acid | 256 |
| 7 | 16 | stearic acid | 284 |
| 8 | 18 | arachidinic acid | 312 |
| 9 | 20 | behenic acid | 340 |

To a suitable reactor equipped with heating and an ability to distill off water is added the specified number of grams of sorbitol (Example 1) is added the specified number of grams of the specified dimer acid (Examples 2-3), next is added the specified number of grams of the specified liquid acid (Examples 4-5). Finally, is added the specified number of grams of the specified solid fatty acid (Examples 6-9). The reaction mass is heated to 180-200° C. and water is distilled off. The reaction mass is kept at this temperature until the acid value becomes vanishingly low. The reaction mass is cooled and used without additional purification.

|  | Sorbitol | | Dimer Acid | | Liquid Acid | | Solid Acid | | |
|---|---|---|---|---|---|---|---|---|---|
| Example | Ex. | Grams | Ex. | Grams | Ex. | Grams | Ex. | Grams | x value |
| 10 | 1 | 54.6 | 2 | 30.0 | 4 | 225.5 | 6 | 204.8 | 1 |
| 11 | 1 | 127.4 | 2 | 150.0 | 4 | 253.6 | 7 | 539.6 | 5 |
| 12 | 1 | 218.4 | 2 | 300.0 | 4 | 394.8 | 8 | 436.8 | 10 |
| 13 | 1 | 400.4 | 2 | 600.0 | 4 | 1353.6 | 9 | 1258.0 | 20 |
| 14 | 1 | 127.4 | 3 | 150.0 | 5 | 225.6 | 6 | 512.0 | 5 |
| 15 | 1 | 218.4 | 3 | 300.0 | 5 | 169.2 | 7 | 1136.0 | 10 |
| 16 | 1 | 54.6 | 3 | 30.0 | 5 | 225.6 | 8 | 249.0 | 1 |
| 17 | 1 | 400.4 | 3 | 600.0 | 5 | 1128.0 | 9 | 1360.0 | 20 |

Ex means example in the table above.

Products that are of the present invention were low order soft pastes that liquefied under pressure. Those products that were made using only solid fatty acids were hard solids that were not spreadable on the skin or hair. Those made without solid fatty acids, but only liquid fatty acids, (oleic and iso stearic) were sticky liquids. Those made with iso-stearic acid were glossy on hair and skin, while those made with oleic acid were emollients.

The compounds are of exceptional interest in the personal care applications where gloss, rheology that accommodates spreading and odor are critical.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

We claim:

1. A polyester that conforms to the following structure:

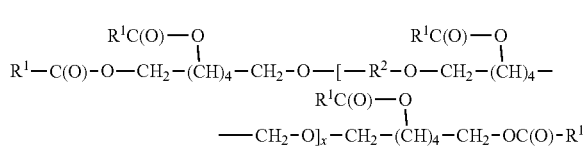

$R^1$ is a mixture of between 15 and 60% —$(CH_2)_a$—$CH_3$ and
between 85 and 40% of fatty acids selected from the group consisting of

—$(CH_2)_8$—CH=CH—$(CH_2)_6$—$CH_3$ and

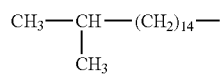

and mixtures thereof;
a is an integer ranging from 14 to 20;
$R^2$ is selected from the group consisting of;

hydrogenated dimer acid, conforming to the following structure:

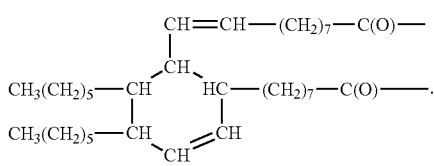

and mixtures thereof;
x is an integer ranging from 1 to 20.

2. A polyester of claim 1 wherein $R^2$

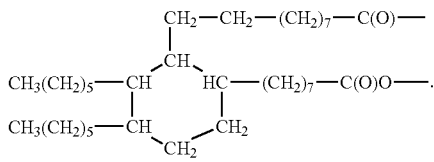

3. A polyester of claim 1 wherein $R^2$

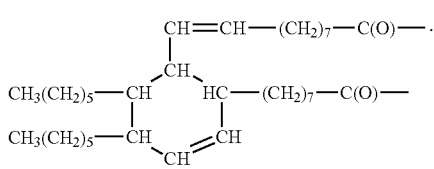

4. A process for conditioning hair and skin which comprises contacting the hair or skin with an effective conditioning concentration of a polyester that conforms to the following structure:

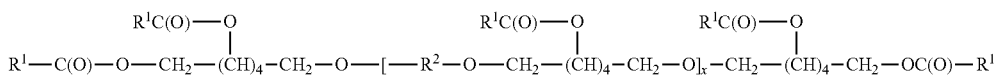

$R^1$ is a mixture of between 15 and 60% —$(CH_2)_a$—$CH_3$ and
between 85 and 40% of fatty acids selected from the group consisting of

—$(CH_2)_8$—CH=CH—$(CH_2)_6$—$CH_3$ and

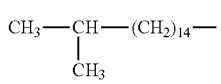

and mixtures thereof;

a is an integer ranging from 14 to 20;
$R^2$ is selected from the group consisting of;

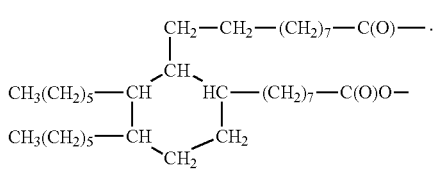

hydrogenated dimer acid, conforming to the following structure:

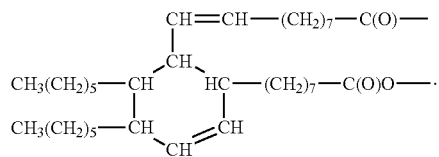

and mixtures thereof;
x is an integer ranging from 1 to 20.

5. A process of claim 4 wherein said effective conditioning concentration ranges from 0.1% to 20% by weight:

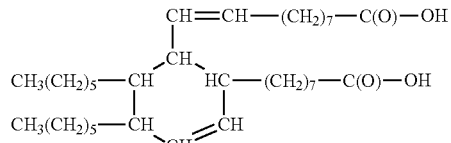

6. A polyester made by the esterification reaction of:
(a) sorbitol conforming to the following structure;

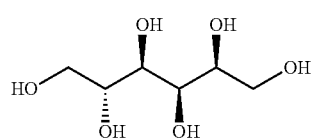

(b) a di acid selected from the group consisting of:

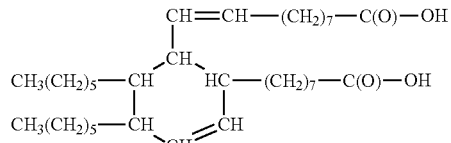

hydrogenated dimer acid, conforming to the following structure:

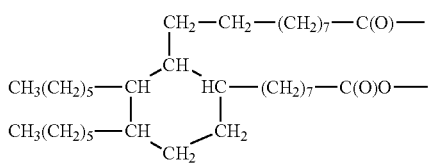

and mixtures thereof;
(c) a fatty acid that is liquid at room temperature, selected from the group consisting of oleic acid conforming to the following structure:

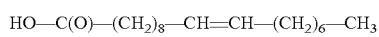

and iso-stearic acid conforming to the following structure:

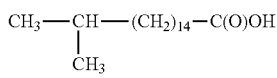

and mixtures thereof;
(d) a fatty acid that is solid at room temperature

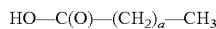

a is an integer ranging from 14 to 20.

7. A polyester made by the esterification reaction of:
(a) sorbitol conforming to the following structure:

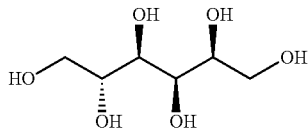

(b) a di acid selected from the group consisting of:

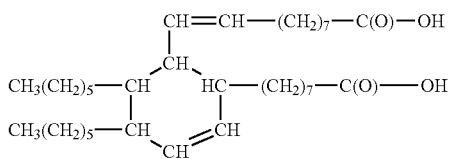

hydrogenated dimer acid, conforming to the following structure:

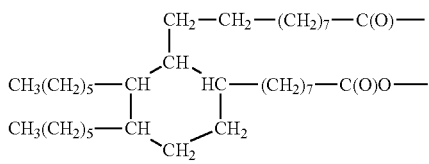

and mixtures thereof;
(c) a fatty acid that is liquid at room temperature, selected from the group consisting of oleic acid conforming to the following structure:

HO—C(O)—(CH$_2$)$_8$—CH=CH—(CH$_2$)$_6$—CH$_3$ and iso-stearic acid conforming to the following structure:

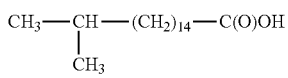

and mixtures thereof;
(d) a fatty acid that is solid at room temperature

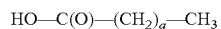

a is an integer ranging from 14 to 20.

8. A process for conditioning hair and skin which comprises contacting the hair or skin with an effective conditioning concentration of a polyester made by the esteritication reaction of:
(a) sorbitol conforming to the following structure:

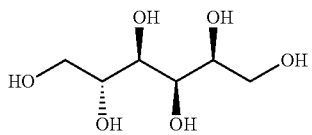

(b) a di acid selected from the group consisting of:

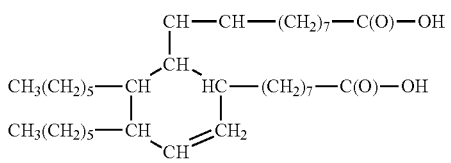

hydrogenated dimer acid, conforming to the following structure:

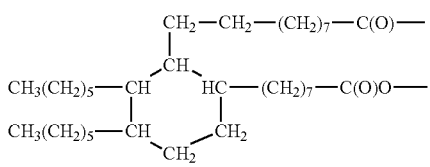

and mixtures thereof;
(c) a fatty acid that is liquid at room temperature, selected from the group consisting of oleic acid conforming to the following structure:

HO—C(O)—(CH$_2$)$_8$CH=CH—(CH$_2$)$_6$—CH$_3$ and iso-stearic acid conforming to the following structure:

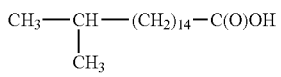

and mixtures thereof;
(d) a fatty acid that is solid at room temperature

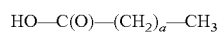

a is an integer ranging from 14 to 20.

* * * * *